United States Patent
Klasner

(10) Patent No.: US 9,182,376 B2
(45) Date of Patent: Nov. 10, 2015

(54) DETERMINING CONSTITUENTS OF A WELLBORE FLUID

(71) Applicant: Halliburton Energy Services, Inc., Houston, TX (US)

(72) Inventor: Scott Anthony Klasner, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 332 days.

(21) Appl. No.: 13/780,068

(22) Filed: Feb. 28, 2013

(65) Prior Publication Data

US 2014/0238114 A1    Aug. 28, 2014

(51) Int. Cl.
*G01N 29/02* (2006.01)
*G01N 29/036* (2006.01)
*E21B 43/26* (2006.01)

(52) U.S. Cl.
CPC ............. *G01N 29/022* (2013.01); *E21B 43/26* (2013.01); *G01N 2291/0226* (2013.01); *G01N 2291/02809* (2013.01)

(58) Field of Classification Search
CPC ............. G01N 29/036; G01N 29/022; G01N 2291/0256; G01N 11/16; G01N 9/002; G01N 2291/0427; G01N 2291/0426; G01N 2291/0422; G01N 2291/014
See application file for complete search history.

(56) References Cited

U.S. PATENT DOCUMENTS

| | | | | |
|---|---|---|---|---|
| 5,201,215 A * | 4/1993 | Granstaff et al. | | 73/54.41 |
| 5,684,276 A * | 11/1997 | Altemir | | 177/210 FP |
| 5,705,399 A * | 1/1998 | Larue | | 436/501 |
| 5,734,098 A * | 3/1998 | Kraus et al. | | 73/61.62 |
| 6,161,420 A * | 12/2000 | Dilger et al. | | 73/24.01 |
| 6,350,609 B1 * | 2/2002 | Morozov et al. | | 506/16 |
| 6,357,278 B1 * | 3/2002 | Sivavec et al. | | 73/24.01 |
| 6,399,575 B1 * | 6/2002 | Smith et al. | | 514/17.7 |
| 6,880,402 B1 * | 4/2005 | Couet et al. | | 73/579 |
| 6,938,470 B2 * | 9/2005 | DiFoggio et al. | | 73/152.24 |
| 7,134,319 B2 * | 11/2006 | Liu | | 73/31.06 |
| 7,219,536 B2 * | 5/2007 | Liu et al. | | 73/54.24 |
| 7,802,466 B2 * | 9/2010 | Whalen et al. | | 73/54.41 |
| 8,802,410 B2 * | 8/2014 | Kack et al. | | 435/181 |
| 8,945,371 B2 * | 2/2015 | Kouznetsov et al. | | 205/793.5 |

(Continued)

FOREIGN PATENT DOCUMENTS

CA    2733135 A1 *    9/2011

OTHER PUBLICATIONS

S.L. Hellstrom, "Introduction to Quartz Crystal Microbalance", Dec. 7, 2007.*

Wink, Thijs et al., "Self-Assembled Monolayers for Biosensors," The Analyst, vol. 122, Apr. 1997, 43R-50R (8 pages).

(Continued)

*Primary Examiner* — David A Rogers
(74) *Attorney, Agent, or Firm* — Craig W. Roddy; Fish & Richardson P.C.

(57) ABSTRACT

Techniques for determining a wellbore fluid constituent concentration include depositing a portion of a hydraulic fracturing fluid that includes a base fluid on a quartz crystal microbalance, the base fluid including a constituent; measuring an oscillation frequency of the quartz crystal microbalance based on the constituent of the base fluid; determining, with the quartz crystal microbalance, a mass of the constituent in the deposited portion of the hydraulic fracturing fluid; and based on at least one of the determined mass or the measured frequency, determining a concentration of the constituent of the base fluid.

22 Claims, 4 Drawing Sheets

(56) References Cited

U.S. PATENT DOCUMENTS

| | | | |
|---|---|---|---|
| 2004/0210099 A1* | 10/2004 | Shiratori | 585/821 |
| 2006/0183165 A1* | 8/2006 | Zhang et al. | 435/7.9 |
| 2008/0139410 A1* | 6/2008 | Chen et al. | 507/204 |
| 2008/0163688 A1* | 7/2008 | Wang et al. | 73/580 |
| 2009/0090504 A1* | 4/2009 | Weightman et al. | 166/250.01 |
| 2010/0251802 A1* | 10/2010 | Patel et al. | 73/19.1 |
| 2012/0211190 A1* | 8/2012 | Goto et al. | 162/198 |
| 2013/0233449 A1* | 9/2013 | Pelletier | 148/241 |
| 2014/0208826 A1* | 7/2014 | Larter et al. | 73/23.41 |

OTHER PUBLICATIONS

Clayton, Lawrence D. et al., "Quartz Thickness-Shear Mode Pressure Sensor Design for Enhanced Sensitivity," IEEE Transactions on Ultrasonics, Ferroelectrics, and Frequency Control, vol. 45, No. 5, Sep. 1998, pp. 1196-1203 (8 pages).

Love, J. Christopher et al., "Self-Assembled Monolayers of Thiolates on Metals as a Form of Nanotechnology," Chem. Rev., vol. 105, No. 4, 2005, pp. 1103-1169 (67 pages).

"Microsensors and Sensor Microsystems," http://www.sandia.gov/mstc/MsensorSensorMsystems/technical-information/QCM-arrays.html, last updated Dec. 2, 2010 (3 pages).

* cited by examiner

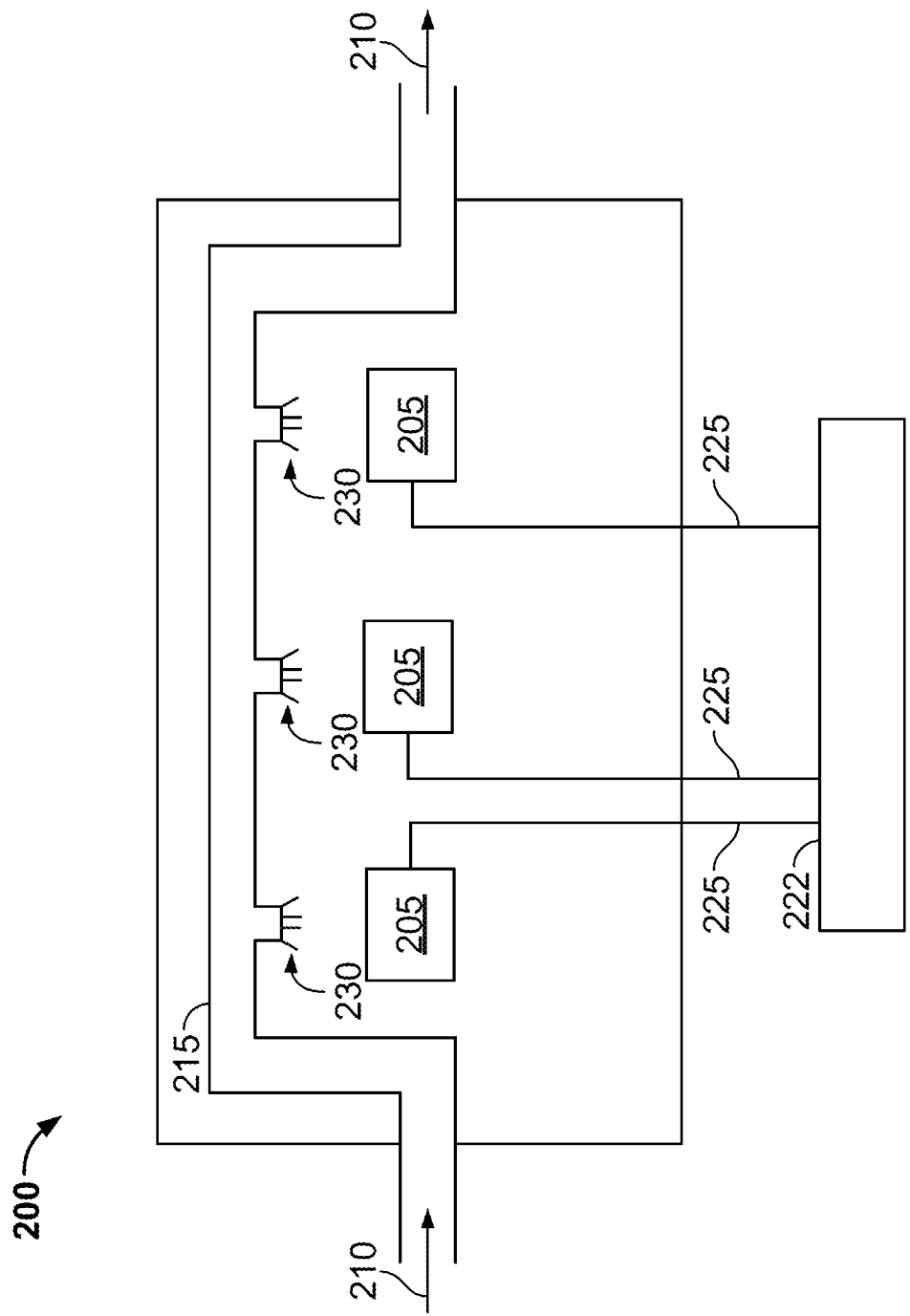

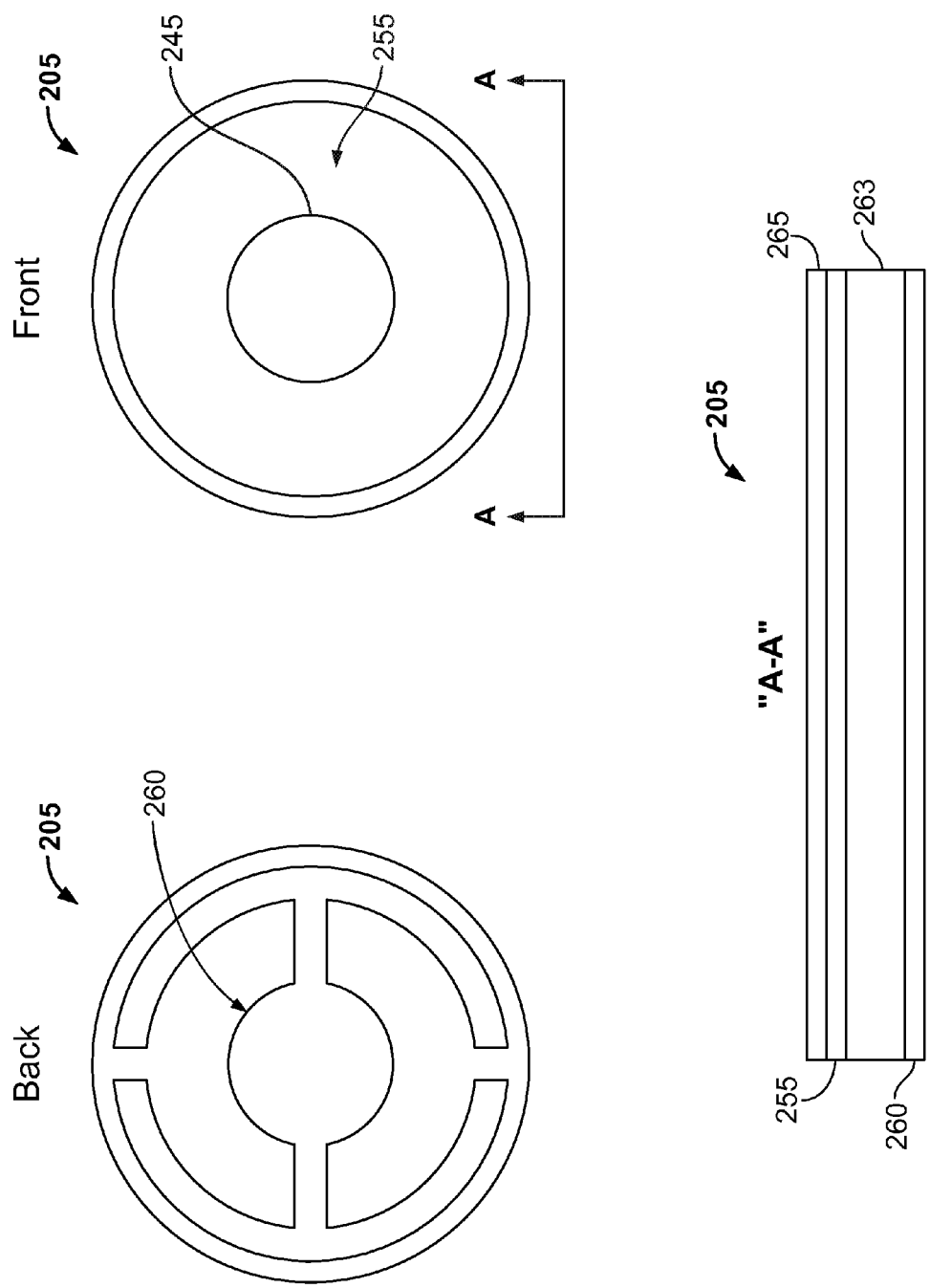

DETERMINING CONSTITUENTS OF A WELLBORE FLUID

TECHNICAL BACKGROUND

This disclosure relates to determining constituents of a wellbore fluid that is distributed through a wellbore.

BACKGROUND

Hydraulic fracturing may be used to increase production of hydrocarbons (e.g., oil, gas, and/or a combination thereof) from one or more subterranean zones. In some cases, a hydraulic fracturing fluid consists of a base fluid, such as water or other liquid, a gel or other liquid comprising one or more fluid additives, such as a cross-linker, a pH stabilizer, and a fluid breaker, and, in some cases, a solid additive such as a proppant. In some cases, for example, due to a lack of readily available base liquid that is uniform in consistency and make-up, the base liquid may be gathered from any readily available source (e.g., ground water source, spring, recycled or reclaimed water source, or otherwise). In some instances, the chemical make-up of the base liquid (e.g., water) varies from source to source.

DESCRIPTION OF DRAWINGS

FIG. 2A illustrates an example constituent sensor that may be utilized in a downhole operation to determine one or more constituents of a wellbore fluid;

FIG. 2B illustrates a detailed view of at least a portion of an example constituent sensor.

DETAILED DESCRIPTION

Figure 1:
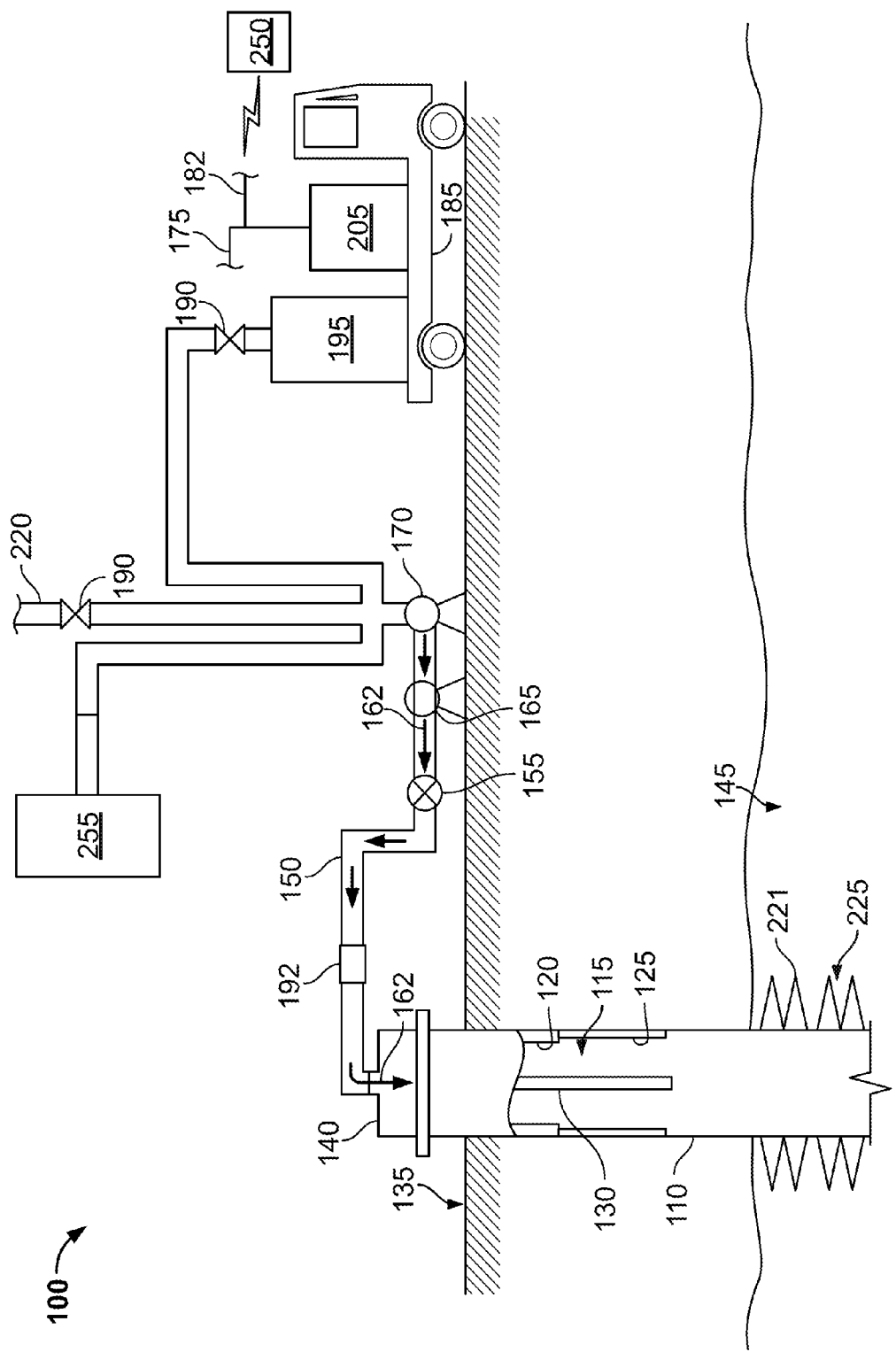
FIG. 1 illustrates an example implementation of at least a portion of a wellsite assembly in the context of a downhole operation (e.g., a fracturing operation)

In one general implementation, a method includes depositing a portion of a hydraulic fracturing fluid that includes a base fluid on a quartz crystal microbalance, the base fluid including a constituent; measuring an oscillation frequency of the quartz crystal microbalance based on the constituent of the base fluid; determining, with the quartz crystal microbalance, a mass of the constituent in the deposited portion of the hydraulic fracturing fluid; and based on at least one of the determined mass or the measured frequency, determining a concentration of the constituent of the base fluid.

A first aspect combinable with the general implementation further includes prior to depositing the portion of the hydraulic fracturing fluid on the quartz crystal microbalance, modifying a surface of the quartz crystal microbalance based on an expected constituent of the base fluid.

In a second aspect combinable with any of the previous aspects, modifying a surface of the quartz crystal microbalance includes functionalizing a gold surface of the quartz crystal microbalance with a moiety that includes a chemical receptor for the expected constituent of the base fluid.

In a third aspect combinable with any of the previous aspects, the determined mass includes a change of an amount of mass calculated with the equation:

$$\Delta m = -\Delta f \frac{A\sqrt{\rho_q \mu_q}}{2f_0^2},$$

where $\Delta m$ is the change in mass of the quartz crystal microbalance as a result of the deposited portion of the hydraulic fracturing fluid, $\Delta f$ is a change in oscillation frequency of the quartz crystal microbalance, $f_0$ is a resonant frequency of the uncoated quartz crystal microbalance, A is a surface area of the quartz crystal microbalance upon which the portion of the hydraulic fracturing fluid is deposited, $\rho_q$ is the density of quartz, and $\mu_q$ is the shear modulus of quartz.

In a fourth aspect combinable with any of the previous aspects, the quartz crystal microbalance includes a first quartz crystal microbalance and a constituent of the base fluid includes a first constituent.

A fifth aspect combinable with any of the previous aspects further includes arranging a second quartz crystal microbalance in series with the first quartz crystal microbalance, the second quartz crystal microbalance including a modified surface based on a second constituent of the base fluid; depositing the portion of the hydraulic fracturing fluid on the second quartz crystal microbalance; measuring an oscillation frequency of the second quartz crystal microbalance based on the second constituent of the base fluid; determining, with the second quartz crystal microbalance, a mass of the second constituent in the deposited portion of the hydraulic fracturing fluid on the second quartz crystal microbalance; and based on at least one of the determined mass of the second constituent or the measured oscillation frequency of the second quartz crystal microbalance, determining a concentration of the second constituent of the base fluid.

In a sixth aspect combinable with any of the previous aspects, the constituent includes (but is not limited to) one or more of a sulfate, an iodide, a borate, an iron, a boron, an aluminum, or a zirconium.

A seventh aspect combinable with any of the previous aspects further includes, prior to depositing a portion of the hydraulic fracturing fluid that includes a base fluid on a quartz crystal microbalance, generating a calibration curve for the quartz crystal microbalance with a predetermined solution that includes the constituent; and determining the concentration of the constituent of the base fluid with the calibration curve.

In an eighth aspect combinable with any of the previous aspects, generating a calibration curve for the quartz crystal microbalance with a predetermined solution that includes the constituent includes contacting a first predetermined solution that includes a first known concentration of the constituent with the quartz crystal microbalance; measuring a first oscillation frequency of the quartz crystal microbalance based on the contact of the first predetermined solution; contacting a second predetermined solution that includes a second known concentration of the constituent with the quartz crystal microbalance; measuring a second oscillation frequency of the quartz crystal microbalance based on the contact of the second predetermined solution; and generating the calibration curve based on the first and second oscillation frequencies and the first and second known concentrations.

In another general implementation, a hydraulic fracturing fluid system includes a base fluid source that includes a base fluid, the base fluid including a constituent; a hydraulic fracturing fluid source that includes a hydraulic fracturing fluid; a mixing assembly fluidly coupled to the base fluid source and to the hydraulic fracturing fluid source; and a constituent sensor in fluid communication with a mixture of the base fluid and the hydraulic fracturing fluid, the constituent sensor including a quartz crystal microbalance, the constituent sensor configured to measure an oscillation frequency of the quartz crystal microbalance based on the constituent of the base fluid and determine the mass of the constituent in the deposited mixture based on the oscillation frequency, and based on at least one of the determined mass of the mixture or the measured oscillation frequency, determine a concentration of the constituent of the base fluid.

In a first aspect combinable with the general implementation, the surface of the quartz crystal microbalance includes a modified surface of the quartz crystal microbalance based on an expected constituent of the base fluid.

In a second aspect combinable with any of the previous aspects, the modified surface of the quartz crystal microbalance includes a functionalized gold surface of the quartz crystal microbalance that includes a moiety of a chemical receptor for the expected constituent of the base fluid.

In a third aspect combinable with any of the previous aspects, the quartz crystal microbalance includes a first quartz crystal microbalance and a constituent of the base fluid includes a first constituent.

In a fourth aspect combinable with any of the previous aspects, the constituent sensor further includes a second quartz crystal microbalance arranged in series with the first quartz crystal microbalance, the second quartz crystal microbalance including a modified surface based on a second constituent of the base fluid, the constituent sensor further configured to determine, based on at least one of the determined mass of the second constituent in the mixture deposited on the modified surface of the second quartz crystal microbalance or a measured oscillation frequency of the second quartz crystal microbalance, a concentration of the second constituent of the base fluid.

In a fifth aspect combinable with any of the previous aspects, the constituent includes (but is not limited to) one or more of a sulfate, an iodide, a borate, an iron, a boron, an aluminum, or a zirconium.

In another general implementation, a method for determining a constituent of a wellbore fluid that includes a constituent includes contacting a portion of the wellbore fluid on a sensor; and determining, with the sensor, a concentration of the constituent of the base fluid based on a measured oscillation frequency of the portion of the wellbore fluid in contact with the sensor.

A first aspect combinable with the general implementation further includes determining the mass of the constituent in deposited portion of the wellbore fluid based on the measured oscillation frequency.

In a second aspect combinable with any of the previous aspects, the oscillation frequency includes a first frequency.

A third aspect combinable with any of the previous aspects further includes prior to contacting the portion of the wellbore fluid on the sensor, measuring a second oscillation frequency of the sensor; determining a difference between the first and second oscillation frequencies; and determining the concentration of the constituent of the base fluid based on the determined difference.

In a fourth aspect combinable with any of the previous aspects, the second oscillation frequency includes a resonant frequency of the sensor.

A fifth aspect combinable with any of the previous aspects further includes contacting another portion of the wellbore fluid on a second sensor; and determining, with the second sensor, a concentration of a second constituent of the base fluid based on a determined mass of the second constituent in the other portion of the wellbore fluid in contact with the second sensor or a measured oscillation frequency of the second sensor in contact with the other portion of the wellbore fluid.

In a sixth aspect combinable with any of the previous aspects, determining the concentration of the constituent of the base fluid and the concentration of the second constituent occur substantially simultaneously.

In a seventh aspect combinable with any of the previous aspects, the sensor includes a quartz crystal microbalance.

Various implementations of systems, method, and apparatus that implement techniques for determining one or more constituents in a wellbore fluid in accordance with the present disclosure may include none, one, some, or all of the following features. For example, a single measurement of a hydraulic fracturing fluid may, simultaneously or substantially simultaneously, provide an indication of multiple constituents of a base hydration fluid of the hydraulic fracturing fluid. Also, the single measurement may be performed, for example, at a wellsite in real time (e.g., almost instantaneously) or near real time (e.g., commiserate with operational speed of hydraulic fracturing equipment) as a hydraulic fracturing operation. In some aspects, this may allow the hydraulic fracturing fluid to be adjusted (e.g., by adjusting the base fluid from one source to another source, metering in particular additives, or otherwise) during the operation. Further, such real time or near real time adjustment may result in more efficient stimulation treatments.

The details of one or more implementations of the subject matter of this disclosure are set forth in the accompanying drawings and the description below. Other features, aspects, and advantages of the subject matter will become apparent from the description, the drawings, and the claims.

FIG. 1 illustrates one implementation of at least a portion of a wellsite assembly 100 in the context of a downhole (e.g., fracturing) operation. A wellbore 110 is formed from a terranean surface 135 to and/or through a subterranean zone 145. The illustrated wellsite assembly 100 includes a tubing system 150 coupled to a flow restriction 155, a pump 165, a mixer 170, a liquid source 220; and a fracturing fluid truck 185 coupled to the tubing system 150. Although illustrated as onshore, the wellsite assembly 100 and/or wellbore 110 can alternatively be offshore or elsewhere. Further, although described in the context of a hydraulic fracturing operation, the wellsite assembly 100 may also illustrate another downhole operation that uses a fluid (e.g., a liquid, slurry, gel, or other fluid) such as an acidizing operation.

In some implementations, all or a portion of the wellsite assembly 100 may facilitate a determination of one or more constituents of a wellbore fluid component. For example, in some aspects, all or a portion of the wellsite assembly 100 may determine one or more constituents of a base fluid (e.g., water or other liquid) used to hydrate a fracturing fluid or gel. In some aspects, as described more fully below, the wellsite assembly 100 may include one or more constituent sensors that, when contacted by a wellbore fluid that includes the base fluid, provides an indication of a concentration of a particular constituent (or constituents) in the base fluid, such as sulfate, iodide, borate, iron, boron, alumina, and zirconium, as some examples. In some aspects, the constituent sensor may include a quartz crystal microbalance that measures a change in oscillation frequency of the quartz crystal based on the contact of the wellbore fluid. The change in oscillation frequency may then be used to determine a mass of the particular constituent in the fluid that is in contact with (e.g., bound to) the quartz crystal microbalance in order to determine a concentration of the particular constituent.

In some implementations, the quartz crystal microbalance may be functionalized according to an expected constituent in the base fluid by, for instance, including a chemical moiety to serve as a receptor for the expected constituent. In one example, the surface of the quartz crystal microbalance can be functionalize (e.g., coated) with a thiol compound to form a self-assembled monolayer of a chemispecific ligand. The thiol compound, in some aspects, would be chosen based on the expected constituent of the base fluid. As another example, in some aspects, the surface of the quartz crystal microbalance may be coated with a polymer coating or other coating (e.g., a cyclodextrin, cavitand, or calixarene) that includes the chemical moiety.

The wellbore 110, at least a portion of which is illustrated in FIG. 1, extends to and/or through one or more subterranean zones under the terranean surface 135, such as subterranean zone 145. Wellbore 110 may allow for production of one or more hydrocarbon fluids (e.g., oil, gas, a combination of oil and/or gas, or other fluid) from, for example, subterranean zone 145. The wellbore 110, in some aspects, is cased with one or more casings. As illustrated, the wellbore 110 includes a conductor casing 120, which extends from the terranean surface 135 shortly into the Earth. Other casing 125 is downhole of the conductor casing 120. Alternatively, some or all of the wellbore 110 can be provided without casing (e.g., open hole). Additionally, in some implementations, the wellbore 110 may deviate from vertical (e.g., a slant wellbore or horizontal wellbore) and/or be a multilateral wellbore.

A wellhead 140 is coupled to and substantially encloses the wellbore 110 at the terranean surface 135. For example, the wellhead 140 may be the surface termination of the wellbore 110 that incorporates and/or includes facilities for installing casing hangers during the well construction phase. The wellhead 140 may also incorporate one or more techniques for hanging tubing 130, installing one or more valves, spools and fittings to direct and control the flow of fluids into and/or from the wellbore 110, and installing surface flow-control facilities in preparation for the production phase of the wellsite assembly 110.

The tubing system 150 is coupled to the wellhead 140 and, as illustrated, provides a pathway for one or more fluids, such as fluid 162, into the wellbore 110. In certain instances, the tubing system 150 is in fluid communication with the tubing 130 extending through the wellbore 110. The fluid 162, in the illustrated implementation of FIG. 1, is a fracturing fluid introduced into the wellbore 110 to generate one or more fractures in the subterranean zone 145.

In the implementation of FIG. 1 illustrating a hydraulic fracturing completion operation, the tubing system 150 is used to introduce the fluid 162 into the wellbore 110 via one or more portions of conduit and one or more flow control devices, such as the flow restriction 155, the pump 165, the mixer 170, one or more valves 190 (e.g., control, isolation, or otherwise), the liquid source 220, and the truck 185. Generally, the pump 165, the mixer 170, the liquid source 220, and the truck 185 are used to mix and pump a fracturing fluid (e.g., fluid 162) into the wellbore 110.

The well assembly 100 includes gel source 195 and solids source 200 (e.g., a proppant source). Either or both of the gel source 195 and solids source 200 could be provided on the truck 185. As used herein, "gel" may include a fluid that is substantially liquid in viscosity as well as a fluid that is of a higher viscosity, such as a gel or other thicker fluid. Although illustrated as a "truck," truck 185 may represent another vehicle-type (e.g., tractor-trailer or other vehicle) or a non-vehicle permanent or semi-permanent structure operable to transport and/or store the gel source 195 and/or solids source 200. Further, reference to truck 185 includes reference to multiple trucks and/or vehicles and/or multiple semi-permanent or permanent structures.

The gel from the gel source 195 is combined with a hydration fluid (e.g., a base fluid), such as water and/or another liquid from the liquid source 220, and additives (e.g., proppant) from a solids source 200 (shown as multiple sources in FIG. 1) in the mixer 170. Proppant, generally, may be particles mixed with fracturing fluid (such as the mixed gel source 195 and liquid source 220) to hold fractures open after a hydraulic fracturing treatment. Proppant may include, for example, naturally occurring sand grains, man-made or specially engineered particles, such as resin-coated sand or ceramic materials like sintered bauxite. Proppant may be selected or specified according to one or more properties, such as, for instance, size, sphericity, density, specific gravity, or otherwise, to provide a path for production of fluid from the subterranean zone 145 to the wellbore 110.

Wellsite assembly 100 also includes a constituent sensor system 192, illustrated in FIG. 1 as in line with, and in fluid communication with, the tubing 150 that carries the wellbore fluid 162. Alternatively, the constituent sensor system 192 may be positioned elsewhere in the wellsite assembly 100 that is in fluid communication with, or can be configured to be in fluid communication with, the wellbore fluid 162. For example, in some aspects, the constituent sensor system 192 may be positioned within the wellsite assembly 100 but not in immediate fluid communication with the wellbore fluid 162 in the tubing 150. For example, the constituent sensor system 192 may be positioned on or near the truck 185 (or other portion of the wellsite assembly 100). At such locations, the constituent sensor system 192 may be positioned to receive a portion of the wellbore fluid 162, either in direct fluid communication through a conduit or by a sample container being of the wellbore fluid 162 brought into proximity with the constituent sensor system 192.

At a high level, the constituent sensor system 192, in some aspects in combination with computing environment 250, may facilitate a determination of one or more constituents of the base fluid (e.g., water or other liquid) from liquid source 220 that is used to hydrate a fracturing fluid or gel. For example, when all or a portion of the constituent sensor system 192 is contacted by the wellbore fluid 162 that includes the base fluid, the constituent sensor system 192 may provide an indication of a concentration of a particular constituent (or constituents) in the base fluid, such as sulfate, iodide, borate, iron, boron, alumina, and zirconium (e.g., through the computing environment 250 or otherwise) as some examples. In some aspects, the constituent sensor system 192 may include a quartz crystal microbalance that measures a change in oscillation frequency of a quartz crystal based on the contact of the wellbore fluid. The change in oscillation frequency may then be used to determine a mass of the analyte (e.g., the particular constituent) in the fluid that is in contact with (e.g., bound to) the quartz crystal microbalance in order to determine a concentration of the particular constituent.

Notably, although the concepts described herein are discussed in connection with a hydraulic fracturing operation, they could be applied to other types of operations. For example, the wellsite assembly could be that of a cementing operation where a cementing mixture (Portland cement, polymer resin, and/or other cementing mixture) may be injected into wellbore 110 to anchor a casing, such as conductor casing 120 and/or surface casing 125, within the wellbore 110. In this situation, the fluid 162 could be the cementing mixture. In another example, the wellsite assembly could be that of a drilling operation, including a managed pressure drilling operation. In another example, the wellsite assembly could be that of a stimulation operation, including an acid treatment. Still other examples exist.

The wellsite assembly 100 also includes computing environment 250 that may be located at the wellsite (e.g., at or near the truck 185) or remote from the wellsite. Generally, the computing environment 250 may include a processor based computer or computers (e.g., desktop, laptop, server, mobile device, cell phone, or otherwise) that includes memory (e.g., magnetic, optical, RAM/ROM, removable, remote or local), a network interface (e.g., software/hardware based interface), and one or more input/output peripherals (e.g., display devices, keyboard, mouse, touchscreen, and others).

In certain implementations, the computing environment 250 may at least partially control, manage, and execute operations associated with determining one or more constituents of a base fluid of wellbore fluid 162. For example, in some aspects, the computing environment 250 may include a power source to supply the constituent sensor system 192 (e.g., a quartz crystal microbalance within the constituent sensor system 192) with a voltage. The computing environment 250 may also measure (e.g., directly or indirectly) an oscillation frequency of the quartz crystal microbalance in the constituent sensor system 192 based on the supplied voltage and contact of the quartz crystal microbalance with the wellbore fluid 162. The computing environment 250 may provide an output (e.g., through a GUI or other output device) of an indication of a type and/or concentration of the one or more constituents of the base fluid. Further, the computing environment 250 may perform one or more calculations to arrive at such output based on, for example, the measure oscillation frequency of the quartz crystal microbalance of the constituent sensor system 192, as described below (e.g., in method 300). In some aspects, the computing environment 250 may control one or more of the illustrated components of well assembly 100 dynamically, such as, in real-time during a fracturing operations at the wellsite assembly 100.

In the illustrated embodiment, the wellbore fluid 162 may be a hydraulic fracturing fluid that forms, e.g., due to pressure, hydraulic fractures 221 in the subterranean zone 145 (shown schematically in FIG. 1). In some aspects, the fractures 221 may increase a permeability of rock in the zone 145, thereby increasing, in some aspects, a flow of hydrocarbon fluids from the zone 145 to the wellbore 110. Fractures 221 may also include, in some aspects, naturally-occurring fractures in the rock of the zone 145. As illustrated, multiple fractures 221 may extend from multiple points of the wellbore 110 and in multiple fracture clusters 225 (e.g., sets of individual fractures 221).

In some examples, each fracture cluster 225 (of which there may be two, more than two, and even many multiple such as hundreds) may be formed, e.g., by a fracture treatment that include pumping the wellbore fluid 162 into the zone 145, at many different levels within the wellbore 145. For example, fracture clusters 225 may be formed at different, specified depths from the terranean surface 135 within the subterranean zone 145 or across multiple subterranean zones 145.

In some aspects, the fracture treatment that includes the wellbore fluid 162 may be a multi-stage treatment. For example, in the multi-stage treatment, a particular zone or length of the wellbore 110 (e.g., all or a portion of a horizontal part of the wellbore 110) may be hydraulically isolated within the wellbore 110 (e.g., with packers or other devices) and a single treatment of the wellbore fluid 162 may be applied to the isolated portion to form multiple fracture clusters 225. In some aspects, the formed fracture clusters 225 may be within a single zone 145 or multiple zones 145.

FIG. 2A illustrates an example constituent sensor assembly 200 that may be utilized in a downhole operation to determine one or more constituents of a wellbore fluid. In some aspects, constituent sensor assembly 200 may be similar to, be used in place of, or be used in addition to, the constituent sensor system 192 shown in the wellsite assembly 100. As illustrated, the constituent sensor assembly 200 includes multiple (e.g., three shown in FIG. 2A but more or fewer are possible) constituent sensors 205, each of which is communicably coupled to a control system 222 through communication lines 225. In some aspects, the control system 222 may be similar to the computing environment 250 shown in FIG. 1. Alternatively, the control system 222 may be a stand-alone controller (e.g., microprocessor-based, PLC, electro-mechanical, or otherwise) that communicates with (e.g., send commands to and/or receives data from) the constituent sensors 205.

Each of the constituent sensors 205 are positioned in the constituent sensor assembly 200 to receive a portion 230 of wellbore fluid 162 from a conduit 210 that carries the wellbore fluid 162. Thus, the constituent sensors 205 are positioned in series to receive the portions 230 simultaneously (e.g., exactly or substantially). Generally, each of the constituent sensors 205 may receive a portion 230 of the wellbore fluid 162 and, in response to contact of the portion 230 with the particular constituent sensor 205 (e.g., a quartz crystal microbalance of the sensor 205), produce a particular output. For instance, in aspects where the constituent sensors 205 each include a quartz crystal microbalance, the particular output may be an output indicating an oscillation frequency associated with the portion 230 in contact with the quartz crystal microbalance. The oscillation frequency output of the constituent sensors 205 may be provided to the control system 220 for determination, for example, of a concentration of a particular constituent of the base fluid of the wellbore fluid 162.

Constituent sensor assembly 200 may, therefore, be operable to determine multiple constituents of the base fluid of the wellbore fluid 162 simultaneously (e.g., substantially or exactly) based on the constituent sensors 205 being placed serially within the assembly 200. For example, in some aspects, a well operator or other operator responsible for a hydraulic fracturing fluid may suspect or expect that a base fluid used to hydrate a hydraulic fracturing fluid (e.g., wellbore fluid 162) may contain several distinct constituents (e.g., sulfate, iodide, borate, iron, boron, alumina, and zirconium). The operator may choose the constituent sensors 205, each of which may be specifically designed for a particular constituent substance. The constituent sensor assembly 200, therefore, may be configured to determine concentrations of different expected constituents. The constituent sensors 205 may, however, be exchanged when different constituents of the base fluid are expected.

FIG. 2B illustrates a more detailed view of at least a portion of the example constituent sensor 205. In this example, the constituent sensor 205 takes the form of a quartz crystal microbalance. Generally, the quartz crystal microbalance 205 is operable to measure a mass per area based on an oscillation frequency of a quartz crystal. In this example, the quartz crystal microbalance 205 includes a front electrode 255 and a back electrode 260, in between which is sandwiched a quartz crystal 263. The quartz crystal microbalance 205 also includes a deposit area 245 on which a portion of a wellbore fluid may be placed (e.g., sprayed, dropped) in contact.

In some aspects, as shown in the side view "A-A," the quartz crystal microbalance 205 may include a functionalized surface 265. The functionalized surface 265 may be configured to bind to a particular, expected constituent (e.g., sulfate, iodide, borate, iron, boron, alumina, and zirconium) of the base fluid. For example, in some aspects, the surface 265 may include a moiety (e.g., a molecule part of a common functional group that may undergo the same or similar chemical reaction(s) as other molecules within the group, regardless of size) that serves as a chemical receptor for the particular, expected constituent.

In operation, a voltage may be applied (e.g., by the control system 220) to the front electrode 255 and the back electrode 260 (which, in some aspects, may be gold) to generate an electric potential across the quartz crystal microbalance 205. The electric potential generates an oscillating electric field that is transverse to the surface 265 of the quartz crystal microbalance 205. Upon contact of the wellbore fluid 162 with the surface 265, the particular constituent of the base fluid binds (e.g., reversibly) to the chemical receptor of the functionalized surface 265 and the quartz crystal 263 may generate a mechanical oscillation due to the piezoelectric effect of the quartz.

This mechanical oscillation can then be measured, and is related to the mass of the particular constituent (or constituents) in the wellbore fluid 162 that is in contact with (e.g., bound to) the surface 265. Once measured, and as described more fully below, the mass of the portion can be determined and the concentration of the particular constituent of the base fluid may be determined.

Figure 3:
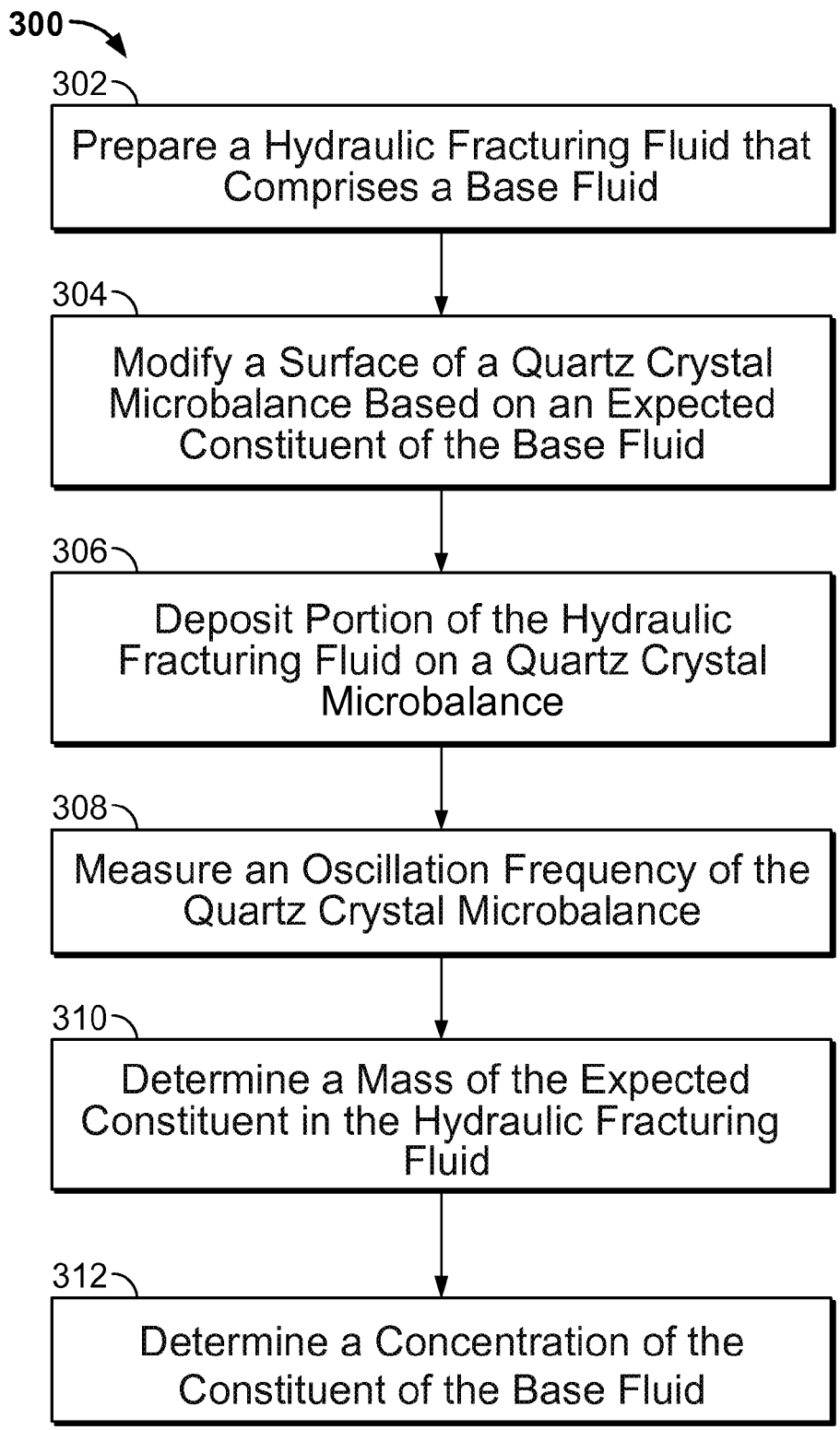
FIG. 3 illustrates an example method for determining one or more constituents of a wellbore fluid.

FIG. 3 illustrates an example method 300 for determining one or more constituents of a wellbore fluid. In some implementations, method 300 may be executed by all or a portion of the wellsite assembly 100 shown in FIG. 1 or, alternatively, another wellsite assembly constructed in accordance with the present disclosure. For example, in some aspects, method 300 may be executed by all or part of the constituent sensor system 192 in combination with, for instance, the computing environment 250 (or other control system or microprocessor-based controller). Further, in some aspects, method 300 may be implemented with one or more of the illustrated constituent assemblies 200 shown in FIGS. 2A-2B.

The illustrated method 300 may begin at step 302, when a wellbore fluid, such as a hydraulic fracturing fluid, may be prepared. The hydraulic fracturing fluid may include, among other fluids or solids, a base fluid. In some aspects, the base fluid is water, such as from a natural body of water, an underground reservoir or aquifer, a manmade storage tank, or other water source. As described above, the base fluid (e.g., water) may provide a hydration source for one or more other components of the hydraulic fracturing fluid such as, for instance, a gel or other fluid that forms the fracturing fluid. In some aspects, the base fluid may include one or more constituents in addition to the molecular make-up of water (e.g., $H_2O$). Such constituents may include, for example, sulfate, iodide, borate, iron, boron, alumina, and zirconium, to name a few.

In step 304, a surface of a quartz crystal microbalance, such as within a constituent sensor or sensor assembly, may be modified based on an expected constituent of the base fluid. For example, in some aspects, a particular base fluid source may have one or more suspected (or expected) constituents, e.g., from sampling, historical data and/or analysis, or otherwise. The surface of the quartz crystal microbalance (e.g., a gold surface) may be functionalized according to the suspected or expected constituents. For instance, in some aspects, the surface may be functionalized with a moiety that serves as a chemical receptor for the suspected or expected constituent.

In step 306, a portion of the hydraulic fracturing fluid (or other wellbore fluid that is used in other wellbore operations) is deposited on the surface of the quartz crystal microbalance. In some aspects, when exposed to the deposited portion of the fracturing fluid, the functionalized surface may bind to a molecule of the expected or suspected constituent (e.g., reversibly or irreversibly).

In step 308, an oscillation frequency of the constituent sensor, (e.g., the quartz crystal microbalance) is measured in response to the deposited portion of the hydraulic fracturing fluid. In some aspects, the measured frequency may be compared against a resonant frequency of an uncoated surface of the quartz crystal microbalance, e.g., the surface without the deposited portion of hydraulic fracturing fluid being placed on it. Thus, a relative oscillation frequency due to the deposited portion of the hydraulic fracturing fluid may be measured.

In step 310, a mass of the constituent in the deposited portion of the hydraulic fracturing fluid (e.g., bound to the sensor) may be determined based on the determined oscillation frequency. In some aspects, the mass may be determined according to a rearranged version of the Sauerbrey equation:

$$\Delta m = -\Delta f \frac{A\sqrt{\rho_q \mu_q}}{2 f_0^2}.$$

where $\Delta m$ is the change in mass (grams) of the quartz crystal microbalance as a result of the deposited portion of the hydraulic fracturing fluid, $\Delta f$ is a change in oscillation frequency (Hz) of the quartz crystal microbalance, $f_0$ is a resonant frequency (Hz) of the uncoated quartz crystal microbalance, $A$ is a surface area (cm$^2$) of the quartz crystal microbalance upon which the portion of the hydraulic fracturing fluid is deposited, $\rho_q$ is the density of quartz (e.g., about 2.648 g/cm$^3$), and $\mu_q$ is the shear modulus of quartz (e.g., about $2.947 \times 10^{13}$ g/cm s$^2$).

In some aspects, the quartz crystal microbalance may be calibrated prior to performing method 300 in order to determine the resonant oscillation frequency of the quartz crystal microbalance with the functionalized surface (e.g., with the moiety that serves as the chemical receptor).

In step 312, a concentration of the constituent is determined based on the determined mass and/or oscillation frequency of the deposited portion of the hydraulic fracturing fluid. For instance, in some aspects, the concentration may be determined based on a calibration curve that is developed, for instance, prior to depositing the portion of the hydraulic fracturing fluid on the quartz crystal microbalance. For example, during calibration of a quartz crystal microbalance that has been functionalized for a particular constituent (e.g., iron), different fluids with known concentrations (e.g., in parts per million ("PPM")) of iron can be deposited, one at a time, on the functionalized quartz crystal microbalance. For each deposit of fluid with the known concentration, an oscillation frequency response can be measured from the quartz crystal microbalance. Thus, a calibration curve of measured oscillation frequency vs. concentration (e.g., 1 PPM, 100 PPM, 10000 PPM, etc.) can be generated. Thus, in step 312, comparison of the measured mass and/or oscillation frequency of the deposited portion and the calibration curve yields a concentration of the particular constituent in the deposited portion.

Method 300 may include other steps. For example, in some implementations, a base fluid (e.g., water) may be tested with a constituent sensor prior to the base fluid being mixed with, for example, a hydraulic fracturing gel or other fracturing chemicals (breakers, crosslinkers, etc.). For example, by testing the base fluid with the constituent sensor (e.g., in steps 306-312), an indication may be provided as to how constituents in the base fluid may affect performance of the fracturing chemicals. With such an indication of a concentration of a particular constituent in the base fluid, alone, determinations can be made as to whether or not to include particular fracturing chemicals (e.g., at particular amounts or concentrations) in the hydraulic fracturing gel.

A number of implementations have been described. Nevertheless, it will be understood that various modifications may be made. For example, advantageous results may be achieved if the steps of the disclosed techniques were performed in a different sequence, if components in the disclosed systems were combined in a different manner, or if the components were replaced or supplemented by other components. Further, in some implementations, one or more method or processes disclosed here, such as, for example, method 300, may be performed with additional steps, fewer steps, or may be performed in different orders than those disclosed herein, within the scope of the present disclosure. Accordingly, other implementations are within the scope of the following claims.

What is claimed is:

1. A method comprising:
   depositing a portion of a base fluid for a hydraulic fracturing fluid on a quartz crystal microbalance, the base fluid comprising a constituent;
   measuring an oscillation frequency of the quartz crystal microbalance based on the constituent of the base fluid;
   determining, with the quartz crystal microbalance, a mass of the constituent in the deposited portion of the base fluid for the hydraulic fracturing fluid;
   based on at least one of the determined mass or the measured frequency, determining a concentration of the constituent of the base fluid; and
   determining, based on the determined concentration of the constituent, an amount or a concentration of an additive to add to the hydraulic fracturing fluid.

2. The method of claim 1, further comprising:
   prior to depositing the portion of the base fluid for the hydraulic fracturing fluid on the quartz crystal microbalance, modifying a surface of the quartz crystal microbalance based on an expected constituent of the base fluid.

3. The method of claim 2, where modifying a surface of the quartz crystal microbalance comprises functionalizing a gold surface of the quartz crystal microbalance with a moiety that comprises a chemical receptor for the expected constituent of the base fluid.

4. The method of claim 1, where the determined mass comprises a change of an amount of mass calculated with the equation:

$$\Delta m = -\Delta f \frac{A\sqrt{\rho_q \mu_q}}{2f_0^2},$$

where $\Delta m$ is the change in mass of the quartz crystal microbalance as a result of the deposited portion of the hydraulic fracturing fluid, $\Delta f$ is a change in oscillation frequency of the quartz crystal microbalance, $f_0$ is a resonant frequency of the uncoated quartz crystal microbalance, A is a surface area of the quartz crystal microbalance upon which the portion of the hydraulic fracturing fluid is deposited, $\rho_q$ is the density of quartz, and $\mu_q$ is the shear modulus of quartz.

5. The method of claim 1, where the quartz crystal microbalance comprises a first quartz crystal microbalance and a constituent of the base fluid comprises a first constituent, the method further comprising:
   arranging a second quartz crystal microbalance in series with the first quartz crystal microbalance, the second quartz crystal microbalance comprising a modified surface based on a second constituent of the base fluid;
   depositing the portion of the base fluid for the hydraulic fracturing fluid on the second quartz crystal microbalance;
   measuring an oscillation frequency of the second quartz crystal microbalance based on the second constituent of the base fluid;
   determining, with the second quartz crystal microbalance, a mass of the second constituent in the deposited portion of the hydraulic fracturing fluid on the second quartz crystal microbalance; and
   based on at least one of the determined mass of the second constituent or the measured oscillation frequency of the second quartz crystal microbalance, determining a concentration of the second constituent of the base fluid.

6. The method of claim 5, further comprising determining, based on the determined concentration of the second constituent, an amount or a concentration of a second additive to add to the hydraulic fracturing fluid.

7. The method of claim 5, further comprising determining, based on the determined concentration of the second constituent, a change to the amount or the concentration of the additive to add to the hydraulic fracturing fluid.

8. The method of claim 1, where the constituent comprises one or more of a sulfate, an iodide, a borate, an iron, a boron, an aluminum, or a zirconium.

9. The method of claim 1, further comprising:
   prior to depositing the portion of the base fluid for the hydraulic fracturing fluid on a quartz crystal microbalance, generating a calibration curve for the quartz crystal microbalance with a predetermined solution that comprises the constituent; and
   determining the concentration of the constituent of the base fluid with the calibration curve.

10. The method of claim 9, where generating a calibration curve for the quartz crystal microbalance with a predetermined solution that includes the constituent comprises:
    contacting a first predetermined solution that comprises a first known concentration of the constituent with the quartz crystal microbalance;
    measuring a first oscillation frequency of the quartz crystal microbalance based on the contact of the first predetermined solution;
    contacting a second predetermined solution that comprises a second known concentration of the constituent with the quartz crystal microbalance;
    measuring a second oscillation frequency of the quartz crystal microbalance based on the contact of the second predetermined solution; and
    generating the calibration curve based on the first and second oscillation frequencies and the first and second known concentrations.

11. A hydraulic fracturing fluid system comprising:
    a base fluid source that comprises a base fluid, the base fluid comprising a constituent;
    a hydraulic fracturing fluid source that comprises a hydraulic fracturing fluid;
    a mixing assembly fluidly coupled to the base fluid source and to the hydraulic fracturing fluid source; and a constituent sensor in fluid communication with the base fluid and the hydraulic fracturing fluid, the constituent sensor comprising a quartz crystal microbalance, the constituent sensor configured to measure an oscillation frequency of the quartz crystal microbalance based on the constituent of the base fluid and determine the mass of the constituent in the deposited mixture based on the oscillation frequency, and based on at least one of the determined mass of the mixture or the measured oscillation frequency, determine a concentration of the constituent of the base fluid and determine, based on the determined concentration of the constituent, an amount or a concentration of an additive to add to the hydraulic fracturing fluid.

12. The hydraulic fracturing fluid system of claim 11, where the surface of the quartz crystal microbalance comprises a modified surface of the quartz crystal microbalance based on an expected constituent of the base fluid.

13. The hydraulic fracturing fluid system of claim 12, where the modified surface of the quartz crystal microbalance comprises a functionalized gold surface of the quartz crystal microbalance that comprises a moiety of a chemical receptor for the expected constituent of the base fluid.

14. The hydraulic fracturing fluid system of claim 11, where the quartz crystal microbalance comprises a first quartz crystal microbalance and a constituent of the base fluid comprises a first constituent, the constituent sensor further comprising:

a second quartz crystal microbalance arranged in series with the first quartz crystal microbalance, the second quartz crystal microbalance comprising a modified surface based on a second constituent of the base fluid, the constituent sensor further configured to determine, based on at least one of the determined mass of the second constituent in the mixture deposited on the modified surface of the second quartz crystal microbalance or a measured oscillation frequency of the second quartz crystal microbalance, a concentration of the second constituent of the base fluid.

15. The hydraulic fracturing fluid system of claim 11, where the constituent comprises one or more of a sulfate, an iodide, a borate, an iron, a boron, an aluminum, or a zirconium.

16. A method for determining a constituent of a wellbore fluid comprising a constituent, the method comprising:
contacting a portion of the wellbore fluid on a sensor; and
determining, with the sensor, a concentration of the constituent of the wellbore fluid based on a measured oscillation frequency of the portion of the wellbore fluid in contact with the sensor; and
based on the determined concentration of the constituent, determining an amount or a concentration of an additive to add to a hydraulic fracturing fluid that comprises the wellbore fluid.

17. The method of claim 16, further comprising:
determining the mass of the constituent in deposited portion of the wellbore fluid based on the measured oscillation frequency.

18. The method of claim 16, where the oscillation frequency comprises a first frequency, the method further comprising:
prior to contacting the portion of the wellbore fluid on the sensor, measuring a second oscillation frequency of the sensor;
determining a difference between the first and second oscillation frequencies; and
determining the concentration of the constituent of the base fluid based on the determined difference.

19. The method of claim 18, where the second oscillation frequency comprises a resonant frequency of the sensor.

20. The method of claim 16, further comprising:
contacting another portion of the wellbore fluid on a second sensor;
determining, with the second sensor, a concentration of a second constituent of the wellbore fluid based on a determined mass of the second constituent in the other portion of the wellbore fluid in contact with the second sensor or a measured oscillation frequency of the second sensor in contact with the other portion of the wellbore fluid; and
based on the determined concentration of the second constituent, determining an amount or a concentration of another additive to add to the hydraulic fracturing fluid that comprises the wellbore fluid.

21. The method of claim 20, where determining the concentration of the constituent of the base fluid and the concentration of the second constituent occur substantially simultaneously.

22. The method of claim 16, where the sensor comprises a quartz crystal microbalance.

* * * * *